(12) United States Patent
Jacobsen et al.

(10) Patent No.: US 6,878,823 B2
(45) Date of Patent: Apr. 12, 2005

(54) 1,2,3,4,5,6-HEXAHYDROAZEPINO[4,5-B] INDOLES CONTAINING ARYLSULFONES AT THE 9-POSITION

(75) Inventors: Eric Jon Jacobsen, Richland, MI (US); Susan Fox Jacobsen, Richland, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 63 days.

(21) Appl. No.: 10/022,471

(22) Filed: Oct. 30, 2001

(65) Prior Publication Data

US 2002/0128475 A1 Sep. 12, 2002

Related U.S. Application Data

(62) Division of application No. 09/613,843, filed on Jul. 11, 2000, now Pat. No. 6,468,449
(60) Provisional application No. 60/144,574, filed on Jul. 19, 1999.

(51) Int. Cl.[7] ............................................. C07D 223/12
(52) U.S. Cl. ..................................................... 540/606
(58) Field of Search ........................................ 540/606

(56) References Cited

U.S. PATENT DOCUMENTS

| | | | |
|---|---|---|---|
| 3,839,357 A | 10/1969 | Hester, Jr. ................. | 260/326.5 |
| 3,576,872 A | 4/1971 | Singhal ...................... | 260/562 |
| 3,652,588 A | 3/1972 | Hester, Jr. ................. | 260/326.3 |
| 3,676,558 A | 7/1972 | Hester, Jr. ................. | 424/274 |
| 3,914,418 A | 10/1975 | Patchett et al. ............ | 424/230 |
| 3,948,987 A | 4/1976 | Fridinger ................... | 260/556 |
| 4,026,830 A | 5/1977 | Gillman et al. ............ | 260/2 P |
| 4,239,888 A | 12/1980 | Miller ........................ | 544/309 |
| 4,298,676 A | 11/1981 | Barton et al. .............. | 430/221 |
| 4,332,820 A | 6/1982 | Markley ..................... | 424/304 |
| 4,894,358 A | 1/1990 | Filosa et al. ................ | 503/201 |
| 5,534,518 A | 7/1996 | Henrie, II et al. .......... | 267/340 |
| 5,952,349 A | 9/1999 | Asberom et al. ........... | 514/316 |

FOREIGN PATENT DOCUMENTS

| | | |
|---|---|---|
| CH | 619 460 A | 9/1980 |
| CZ | 149 525 B | 7/1973 |
| CZ | CS 229 033 B | 5/1984 |
| DE | 21 20 708 | 11/1972 |
| DE | 24 38 099 | 2/1976 |
| DE | 24 38 120 | 2/1976 |
| DE | 25 09 037 | 9/1976 |
| DE | 25 48 910 | 5/1977 |
| DE | 27 07 784 | 8/1977 |
| DE | 27 48 978 | 5/1979 |
| DE | 30 27 530 | 2/1982 |
| DE | 38 31 445 | 3/1990 |
| DE | 196 54 445 | 7/1998 |
| DE | 198 29 357 | 1/2000 |
| EP | 0 013 414 | 7/1980 |
| EP | 0 017 883 | 10/1980 |
| EP | 0 028 381 | 5/1981 |
| EP | 0 035 712 | 9/1981 |
| EP | 0 102 476 | 3/1984 |
| EP | 0 282 448 | 9/1988 |
| EP | 0354 303 A | 2/1990 |
| EP | 0 524 781 | 1/1993 |
| EP | 666 253 A1 | 8/1995 |
| EP | 0 930 302 | 7/1999 |
| FR | 1 489 916 | 11/1967 |
| FR | 1 499 717 | 11/1967 |
| FR | 6 699 M | 2/1969 |
| FR | 2 053 028 | 4/1971 |
| FR | 2 110 283 | 6/1972 |
| FR | 2 135 740 | 12/1972 |
| FR | 2 154 568 A | 5/1973 |
| FR | 2 230 354 | 12/1974 |
| GB | 1293540 | 10/1972 |
| JP | 02 048564 | 2/1980 |
| JP | 60 044557 | 3/1985 |
| JP | 3056431 | 3/1991 |
| RU | 436 817 T | 7/1974 |
| SU | 380644 | 5/1973 |
| SU | 475382 | 6/1975 |

(Continued)

OTHER PUBLICATIONS (Abstract) XP–002150015—J. Med. Chem. (1969), 12, 709–11. Antimalarial compounds related to diaminodiphenyl sulfone; Henry Bader, et al.

(Abstract) XP–002150014 –Macromolecules (1988), 21 (8), 2644–7 A novel route to polypyrazoles; James A. Moore, et al.

(Abstract) XP–002150013—Khim. Geterotsikl. Soedin. (1991),(1) 54–6 Synthesis of 5–[(p–chlorophenyl) sulfonyl] indoles; N.T. Mirziashvili, et al.

(Continued)

*Primary Examiner*—Brenda Coleman
(74) *Attorney, Agent, or Firm*—Charles W. Ashbrook; Mary J. Hosley

(57) ABSTRACT

The present invention are substituted 9-arylsulfone-1,2,3,4, 5,6-hexahydroazepino[4,5-b]indoles (X) and unsubstituted 9-arylsulfone-1,2,3,4,5,6-hexahydroazepino[4,5-b]indoles (XI) such as the compound of EXAMPLE 13

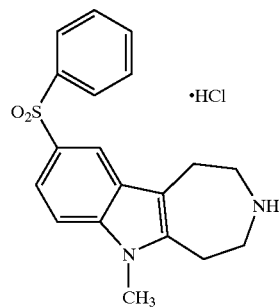

which are useful in treating depression, obesity and other CNS disorders.

2 Claims, No Drawings

FOREIGN PATENT DOCUMENTS

| | | |
|---|---|---|
| WO | WO94/18980 | 9/1994 |
| WO | WO97/13748 | 4/1997 |
| WO | WO99/32463 | 7/1999 |
| WO | WO99/44618 | 9/1999 |
| WO | WO 99/62506 | 12/1999 |
| ZA | 6 801 404 1 | 8/1968 |
| ZA | 7 603 751 A | 2/1978 |

OTHER PUBLICATIONS (Abstract) XP–002150011—J. Chem. Eng. Data (1966), 11(4), 612–14; o–Trifluoromethylthiophenol and its derivatives; N. Sharghi, et al.

(Abstract) XP–002150010—Synthesis (1971), (7), 372–4; Aminoaryl sulfones. New preparation procedure; Everett E. Gilbert.

(Abstract) XP–002150009—J. Med. Chem. (1971), 14(12), 1166–9; Antimalarial agents. 8. Ring–substituted bis (4–aminophenyl) sulfones and their precursors; Ivan C. Popoff, et al.

(Abstract) XP–002150008—ZH. Prikl. Khim. (Leningrad) (1972), 45(12), 2704–10, Synthesis f som substituted diphenyl sulfones; I.V. Budnii, et al.

(Abstract) XP002150007—J. Mol. Struct. (1973), 16(2), 299–306, NMR data and conf rmati nal preference f o–substituted diphenyl sulf nes; G. Montaud , et al.

(Abstract) XP001150005—ZH., Khim. 1973, TR. Vses. Nauch–issled. Proekt. Inst. Monomerov (1972), 3(3), 75–80; Synthesis of 3,4,4'–triaminodipheny sulfones and their use in modifying heat–stable fibers; A.V. Ivanov, et al.

(Abstract) XP002150003—Acta Cienc. Indica (1977), 3(1), 18–19; Fries rearrangement of N–benzenesulfonylaniline; C. Srinivasan.

(Abstract) XP002150002—Khim. Geterotsikl. Soedin (1979), (7) 968–71; Synthesis and study of some bis (1', 8'–naphthoylene–1,2–benzimidazoles); A.L. Rusanov, et al.

(Abstract) XP002150001—Katalitich. Prevrashcheniya Organ. Soedin., Perm (1978) 20–5; Sulfarylation of p–substituted benzenesulfonic acid salts rin phosphoric acid; A. G. Klein, et al.

(Abstract) XP00215000—Quant. Struct.–Act. Relat. (1987), 6(4), 164–72; Multiple regression analysis of antimalarial activities of sulfones and sulfonamides in cell–free systems and principal component analysis to compare with antibacterial activities; M. Wiese, et al.

(Abstract) XP002149999—J. Med. Chem. (1989), 32(10), 2396–9; Quantitative structure–activity relationships in dihydropteroate synthase inhibition by multisubstituted sulfones. Design and synthesis of some new derivatives with improved potency; G. Pier De Benedetti, et al.

(Abstract) XP002149998—Arzneim.–Forsch. (1989), 39(9), 1081–4; Studies on 2,3,N,N'–substituted 4,4'– diaminodiphenylsulfones as potential antimalarian agents; M. Saxena, et al.

(Abstract) XP002149997—J. Clin. Invest. (1990), 85(2), 371–9; Interaction of sulfonamide and sulfone compounds with Toxoplasma gondii dihydropteroate synthase; Carmen J. Allegra, et al.

(Abstract) XP002149996—Theochem (1992), 88, 231–48; Electrostatics in quantitative structure–activity relationship analysis; P.G. De Benedetti.

(Abstract) XP002149995—J. Chem.Soc., Kerkin Trans. 1 (1992), (22), 3129–34; 2H–Benzimidazoles (isobenzimidazoles). Brian Iddon, et al.

(Abstract) XP002149994—Boll. Chim. Farm. (1994), 133(2), 72–5; Synthesis and antimicrobial evaluati n of new derivatives of diphenylsulfone; A. De La Cruz, et al.

(Abstract) XP002149993—Environ. Toxicol. Pharmacol (1998) 5(2), 145–153; The effect of 2,2'–substitution n the metabolism and toxicity of dapsone in vitro and in vivo; M.D. Tingle, et al.

(Abstract) XP002149992—Bol. Soc. Chil. Quim (2000), 45(2), 181–189; Synthesis characterization and electrical properties of poly (p–phenylsulfonyl aniline); Fernando R. Diaz, et al.

(Abstract) XP002149991—Indian J. Appl. Chem. (1966), 29(2–3), 51–3; Potential fungicidal compounds. IV. Some aryl polynitrophenyl sulfones; Satya Prakash Gupta, et al.

(Abstract) XP002149990—J. Chem. Soc. C. (1968), (3), 322–7; Photochemical transformations. XXII. Reactions of 2,4–dinitrobenzenesulfenyl derivatives; Derek H. R. Barton, et al.

(Abstract) XP002149989—ZH. Fiz, Khim. (1968), 42(8), 1861–4; Interaction of functional groups through.pi.–electron systems. V. Interaction through aromatic rings connected by a monofunctional bridging group; A.E. Lutskii, et al.

(Abstract) XP002149987—Ann. Soc. Sci. Bruxelles, Ser. 1 (1969); New phenothiazines by Smiles arrangement; R.L. Mital, et al.

(Abstract) XP002149986—J. Chem. Soc., Perkin Trans. 1 (1973), (18), 1980–3; .sigma.–Complex formulati n and aromatic substitution thiolates and nitroatyl thio ethers; Gino Biggi, et al.

(Abstract) XP–002149983—J. Org. Chem. (1995), 40(25), 3777–8; Electronic and steric effects in nucleophilic aromatic substitution. Kinetic studies on the reactions between ethers and thioethers of 2,4–dinitrophenol and nucleophiles; G. Bartoli, et al.

(Abstract) XP002149981—Chim. Acta. Turc. (1981), 9(2), 395–9; Synthesis and fungitoxicity of some substituted aryl polynitrophenyl sulfies and sulfones; Merra Katiyar, et al.

(Abstract) XP002149979—Khim. Geterotsikl. Soedin. (1968), (1), 131–6; Indole derivatives. XXIV. Synthesis of some 1,2,3,4,5,6–hexahydroazepino [4,5–b]indoles; N.M. Sharkova, et al.

(Abstract) XP002149978—Farmakol. Toksikol (Moscow) (1972), 35(3), 274–80; Pharmacological activity spectra of some azepino–and benzoxepinoindole derivatives; G. N. Artemenko, et al.

XP000650781—Journal of Medicinal Chemistry, US, American Chemical Society, Washington. vol. 11, No. 1, 1968, pp. 101–106; Azepinoindoles. I. Hexahydroazepino [4,5–b]indoles; J. B. Hester, et al.

1,2,3,4,5,6-HEXAHYDROAZEPINO[4,5-B] INDOLES CONTAINING ARYLSULFONES AT THE 9-POSITION

CROSS-REFERENCE TO RELATED APPLICATIONS

The present application is a divisional of U.S. patent application Ser. No. 09/613,843, filed 11 Jul. 2000, now U.S. Pat. No. 6,468,449, which claims the benefit of U.S. provisional Application Ser. No. 60/144574, filed Jul. 19, 1999.

BACKGROUND OF THE INVENTION

1. Field of the Invention

The present invention is substituted 9-arylsulfone-1,2,3,4,5,6-hexahydroazepino[4,5-b]indoles (X) which are useful for treating anxiety, depression and other CNS disorders in humans and animals.

2. Description of the Related Art

U.S. Pat. No. 3,652,588 discloses 6-alkyl-1,2,3,4,5,6-hexahydroazepino[4,5-b]indoles which were useful for tranquilizing and sedating mammals to suppress hunger in mammals. This document discloses that there can be substitution at the 9-position. However, those substituents are limited to hydrogen, alkyl, alkoxy and halogen.

U.S. Pat. No. 3,839,357 discloses 6-benzyl-1,2,3,4,5,6-hexahydroazepino[4,5-b]indoles which were useful for tranquilizing mammals. This document discloses that there can be substitution at the 9-position. However, those substituents are limited to hydrogen, alkyl, alkoxy and halogen.

U.S. Pat. No. 3,676,558 discloses 6-alkyl-1,2,3,4,5,6-hexahydroazepino[4,5-b]indoles which were useful to suppress hunger in mammals. This document discloses that there can be substitution at the 9-position. However, it is limited to hydrogen, alkyl, alkoxy and halogen.

SUMMARY OF INVENTION

Disclosed is a 9-arylsulfone of the formula (XII)

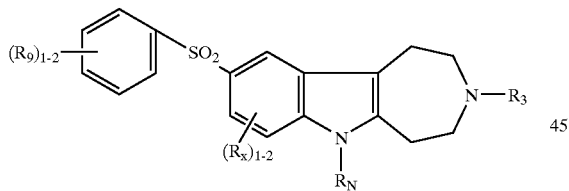

where $R_3$ is:
(1) —H,
(2) $C_1$–$C_4$ alkyl,
(3) $C_0$–$C_4$ alkyl-φ where the -φ substituent is optionally substituted with 1 or 2
 (a) —F, —Cl, —Br, —I,
 (b) —O—$R_{3-1}$ where $R_{3-1}$ is:
  —H,
  $C_1$–$C_4$ alkyl,
  -φ,
 (c) —$CF_3$,
 (d) —CO—$NR_{3-2}R_{3-3}$ where $R_{3-2}$ and $R_{3-3}$ are —H and $C_1$–$C_4$ alkyl, and where $R_{3-2}$ and $R_{3-3}$ are taken with the attached nitrogen atom to form a ring selected from the group consisting of 1-pyrrolidinyl, 1-piperazinyl and 1-morpholinyl,
 (e) —NH—$SO_2$—$R_{3-4}$ where $R_{3-4}$ is —H and $C_1$–$C_4$ alkyl,
 (f) —$NR_{3-2}R_{3-3}$ where $R_{3-2}$ and $R_{3-4}$ are as defined above,
 (g) —$NR_{3-4}$—CO—$R_{3-4}$ where $R_{3-4}$ is as defined above,
 (h) —$SO_2$—$NR_{3-2}R_{3-3}$ where $R_{3-2}$ and $R_{3-3}$ are as defined above,
 (i) —C≡N,
 (j) —$NO_2$,
where $R_N$ is:
(1) —H,
(2) $C_1$–$C_4$ alkyl,
(3) $C_0$–$C_4$ alkyl-φ where the -φ substituent is optionally substituted with 1 or 2
 (a) —F, —Cl, —Br, —I,
 (b) —O—$R_{N-1}$ where $R_{N-1}$ is
  —H,
  $C_1$–$C_4$ alkyl,
  -φ,
 (c) —$CF_3$,
 (d) —CO—$NR_{N-2}R_{N-3}$ where $R_{N-2}$ and $R_{N-3}$ are —H and $C_1$–$C_4$ alkyl, and where $R_{3-2}$ and $R_{3-3}$ are taken with the attached nitrogen atom to form a ring selected from the group consisting of 1-pyrrolidinyl, 1-piperazinyl and 1-morpholinyl,
 (e) —NH—$SO_2$—$R_{N-4}$ where $R_{N-4}$ is —H and $C_1$–$C_4$ alkyl,
 (f) —$NR_{N-2}R_{N-3}$ where $R_{N-2}$ and $R_{N-3}$ are as defined above,
 (g) —$NR_{N-4}$—CO—$R_{N-4}$ where $R_{N-4}$ is as defined above,
 (h) —$SO_2$—$NR_{N-2}R_{N-3}$ where $R_{N-2}$ and $R_{N-3}$ are as defined above,
 (i) —C≡N,
 (j) —$NO_2$,
where $R_X$ is:
(1) —H
(2) —F, —Cl, —Br, —I,
(3) —O—$R_{X-1}$ where $R_{X-1}$ is:
 —H,
 $C_1$–$C_4$ alkyl,
 -φ,
(4) —$CF_3$,
(5) —CO—$NR_{X-2}R_{X-3}$ where $R_{X-2}$ and $R_{X-3}$ are —H and $C_1$–$C_4$ alkyl, and where $R_{X-2}$ and $R_{X-3}$ are taken with the attached nitrogen atom to form a ring selected from the group consisting of 1-pyrrolidinyl, 1-piperazinyl, 1-morpholinyl,
(6) —NH—$SO_2$—$R_{X-4}$ where $R_{X-4}$ is —H and $C_1$–$C_4$ alkyl,
(7) —$NR_{X-2}R_{X-3}$ where $R_{X-2}$ and $R_{X-3}$ are as defined above,
(8) —$NR_{X-4}$—CO—$R_{X-4}$ where $R_{X-4}$ is as defined above,
(9) —$SO_2$—$NR_{X-2}R_{X-3}$ where $R_{X-2}$ and $R_{X-3}$ are as defined above,
(10) —C≡N,
(11) —$NO_2$;
where $R_9$ is:
(1) —H,
(2) —F, —Cl,
(3) $C_1$–$C_4$ alkyl,
(4) $C_1$–$C_3$ alkoxy,
(5) —$CF_3$,
(6) $C_0$–$C_4$ alkyl -φ where the -φ substituent is optionally substituted with 1 or 2

(a) —F, —Cl, —Br, —I,
(b) —O—$R_{9-1}$ where $R_{9-1}$ is:
  —H,
  $C_1$–$C_4$ alkyl,
  -φ,
(c) —$CF_3$,
(d) —CO—$NR_{9-2}R_{9-3}$ where $R_{9-2}$ and $R_{9-3}$ are —H and $C_1$–$C_4$ alkyl, and where $R_{9-2}$ and $R_{9-3}$ are taken with the attached nitrogen atom to form a ring selected from the group consisting of 1-pyrrolidinyl, 1-piperazinyl and 1-morpholinyl,
(e) —NH—$SO_2$—$R_{9-4}$ where $R_{9-4}$ is —H and $C_1$–$C_4$ alkyl,
(f) —$NR_{9-2}R_{9-3}$ where $R_{9-2}$ and $R_{9-3}$ are as defined above,
(g) —$NR_{9-4}$—CO—$R_{9-4}$ where $R_{9-4}$ is as defined above,
(h) —$SO_2$—$NR_{9-2}R_{9-3}$ where $R_{9-2}$ and $R_{9-3}$ are as defined above,
(i) —C≡N,
(j) —$NO_2$
(7) —$OR_{9-1}$ where $R_{9-1}$ is as defined above,
(8) —CO—$NR_{9-2}R_{9-3}$ where $R_{9-2}$ and $R_{9-3}$ are as defined above,
(9) —$NR_{9-2}R_{9-3}$ where $R_{9-2}$ and $R_{9-3}$ are as defined above,
(10) —NH—$SO_2$—$R_{9-4}$ where $R_{9-4}$ is as defined above,
(11) —NH—$CO_2$—$R_{9-2}$ where $R_{9-2}$ is as defined above,
and pharmaceutically acceptable salts thereof.

Also disclosed are compounds which are intermediates in the production of the 9-arylsulfones (XII), the thio ethers of formula (III), the amines of formula (IV), the hydrazines of formula (V), the compounds of formula (VII) and the protected 9-arylsulfones of formula (VIII) where PG is selected from the group consisting of φ-$CH_2$—, φ-CO—, φ-$CH_2$—$CO_2$— and —CO—O—C$(CH_3)_3$ and where $R_9$ and $R_x$ are as defined above.

Further disclosed is a method of treating a human who has a condition selected from the group consisting of anxiety, depression, schizophrenia, stress related disease, panic, a phobia, obsessive compulsive disorder, obeisity, post-traumatic stress syndrome who is in need of such treatment which comprises administering an effective amount of a 9-arylsulfone of the formula (XII).

DETAILED DESCRIPTION OF THE INVENTION

The unsubstituted 9-arylsulfones (IX) and substituted 9-arylsulfones (X) are both prepared by means known to those skilled in the art. The term 9-arylsulfones (XII) includes both the unsubstituted 9-arylsulfones (IX), where $R_3$ is —H and substituted 9-arylsulfones (X) where $R_3$ is ≠ to —H. The process of preparation can be viewed as being in two parts. The first part is the production of the appropriately substituted hydrazone (V), see CHART A. The second part is the coupling and reaction of the appropriately substituted hydrazone (V) with the 1-protected hexahydro-4H-azepine-4-one (VI) to give the intermediate (VII) and its transformation to the unsubstituted 9-arylsulfone (IX), see CHART B.

The appropriately substituted thiols (I) are either known to those skilled in the art or can be readily prepared from known starting materials by means well known to those skilled in the art. There can be either one or two $R_9$ substituents and $R_9$ includes —H, —F, —Cl, $C_1$–$C_3$ alkyl, $C_1$–$C_3$ alkoxy and —$CF_3$; it is preferred that $R_9$ is —H, —F, —Cl, $C_1$ alkyl, $C_1$ alkoxy, and —$CF_3$ and when F— it is preferred that it be in the 4- or p-position. It is preferred that the $R_9$ substituent be in either the 3- or 4-position.

The appropriately substituted thiol (I) is coupled with the appropriately substituted 4-chloro-1-nitrobenzene (II) by known means to produce the thioether (III). There can be either one or two $R_x$ groups. If $R_x$ is other than —H, it should be part of the 4-chloro-1-nitrobenzene (II) so that it will become part of the final unsubstituted 9-arylsulfone (IX) when it is formed. It is most difficult to add the $R_x$ substitutent (other than —H) to the unsubstituted 9-arylsulfone (IX) once it is formed. Therefore, the $R_x$ group should be part of the appropriately substituted 4-chloro-1-nitrobenzene (II) when it is reacted with the thiol (I). $R_x$ includes of —H, —F and —Cl; it is preferred that $R_x$ is —H. The thioether (III) is then oxidized with hydrogen peroxide (30%) followed by reduction with rhodium on carbon (5%), all of which is known to those skilled in the art, to produce the amine (IV). The amine (IV) is then diazotized by (sodium) nitrite and (hydrochloric) acid followed by reduction with tin chloride/water to give the corresponding hydrazine (V).

The second part of the reaction, is well known to those skilled in the art, see U.S. Pat. Nos. 3,652,588, 3,676,558 and 3,839,357. The only difference between the process in those patents and that here is the arylsulfone substituent at the 9-position. That substituent is already in place in the hydrazine (V) prior to the reaction of the 9-arylsulfone hydrazine (V) with the 1-protected hexahydro-4H-azepine-4-one (VI) to produce the correspondingly substituted intermediate (VII). Suitable protecting groups (PG) include φ-$CH_2$—, φ-CO—, φ-$CH_2$—$CO_2$— and —CO—O—C$(CH_3)_3$; it is preferred that the protecting group be φ-$CH_2$— or φ-CO—. The cyclization of the intermediate (VII) to the corresponding protected arylsulfone (VIII) and then the deprotection to the unsubstituted 9-arylsulfone (IX) all follow known methods. The protecting groups (PG) are readily removed by means well known to those skilled in the art. The unsubstituted 9-arylsulfone (IX) can then be substituted at the C3-position ($R_3$, ring nitrogen atom) as well as on the indole nitrogen ($R_N$) as is known to those skilled in the art. Alternatively, arylsulfone (VIII) can be alkylated with the desired $R_N$—X substituent to give the protected indole (XI) which then is deprotected to give the desired substituted 9-arylsulfone (X). Useful $R_3$ groups include of —H and $C_1$–$C_2$ alkyl; it is preferred that $R_3$ be —H. Useful $R_N$ groups include of —H and $C_1$–$C_4$ alkyl; it is preferred that $R_N$ is —H, $C_1$ alkyl and $C_2$ alkyl. The invention here is not the process chemistry but rather the novel products produced.

The preferred protecting group for the intermediates (VI), (VII) and (VIII) are benzyl and benzamide though other groups are operable as is known to those skilled in the art.

The 9-arylsulfones (XI) are amines, and as such form acid addition salts when reacted with acids of sufficient strength. Pharmaceutically acceptable salts include salts of both inorganic and organic acids. The pharmaceutically acceptable salts are preferred over the corresponding free amines since they produce compounds which are more water soluble and more crystalline. The preferred pharmaceutically acceptable salts include salts of the following acids methanesulfonic, hydrochloric, hydrobromic, sulfuric, phosphoric, nitric, benzoic, citric, tartaric, fumaric, maleic, $CH_3$—$(CH_2)_n$—COOH where n is 0 thru 4, HOOC—$(CH_2)_n$—COOH where n is as defined above.

The 9-arylsulfones (XI) of the present invention are useful to treat anxiety, depression, schizophrenia, stress related disease, panic, a phobia, obsessive compulsive disorder, obeisity, post-traumatic stress syndrome and other CNS disorders. It is preferred that the 9-aryl sulfones (XI) be used to treat anxiety for depression. To treat these diseases the 9-arylsulfones (XI) are administered orally, sublingually, transdermally or parenterally to provide a dosage of about 0.1 to about 50 mg/kg/day. It is preferred that the dosage range be from about 0.1 to about 10 mg/kg/day. The 9-arylsulfones (XI) can be administered in divided doses either two, three or four times daily. It is preferred that the 9-arylsulfones (XI) be administered orally.

The exact dosage and frequency of administration depends on the particular 9-arylsulfone(s) used, the particular disease being treated, the severity of the disease being treated, the age, weight, general physical condition of the particular patient, other medication the individual may be taking as is well known to those skilled in the art and can be more accurately determined by measuring the blood level or concentration of the 9-arylsulfone (XI) in the patient's blood and/or the patient's response to the particular condition being treated.

DEFINITIONS AND CONVENTIONS

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)$H. Groups $R_i$ and $R_j$ would represent monovalent variable substituents if attached to the formula $CH_3$—$CH_2$—$C(R_i)(R_j)$—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—$(CH_2)_2$—N($C_2H_5$)—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha (α) configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta (β) configuration and is indicated by an unbroken or solid line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—) or as two separately attached monovalent variable substituents a-$R_{i-j}$ and β-$R_{i-k}$. When a bivalent variable, $R_i$ is defined to consist of two monovalent variable substituents, the convention used to define the bivalent variable is of the form "a-$R_{i-j}$:β-$R_{i-k}$" or some variant thereof. In such a case both a-$R_{i-j}$ and β-$R_{i-k}$ are attached to the carbon atom to give —C(a-$R_{i-j}$)(β-$R_{i-k}$)—. For example, when the bivalent variable $R_6$, —$C(=R_6)$— is defined to consist of two monovalent variable substituents, the two monovalent variable substituents are a-$R_{6-1}$:β-$R_{6-2}$, . . . a-$R_{6-9}$:β-$R_{6-10}$, etc, giving —C(a-$R_{6-1}$)(β-$R_{6-2}$)—, . . . —C(a-$R_{6-9}$)(β-$R_{6-10}$)—, etc. Likewise, for the bivalent variable $R_{11}$, —$C(=R_{11})$—, two monovalent variable substituents are a-$R_{11-1}$:β-$R_{11-2}$. For a ring substituent for which separate a and β orientations do not exist (e.g. due to the presence of a carbon carbon double bond in the ring), and for a substituent bonded to a carbon atom which is not part of a ring the above convention is still used, but the a and β designations are omitted.

Just as a bivalent variable may be defined as two separate monovalent variable substituents, two separate monovalent variable substituents may be defined to be taken together to form a bivalent variable. For example, in the formula —$C_1(R_i)$H—$C_2(R_j)$H— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation " . . . $R_i$ and $R_j$ are taken together to form —$CH_2$—$CH_2$—O—CO— . . . " means a lactone in which the carbonyl is bonded to $C_2$. However, when designated " . . . $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and ($C_1$–$C_3$)alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. Definitions

All temperatures are in degrees Centigrade.

HPLC refers to high pressure liquid chromatography.

DMSO refers to dimethylsulfoxide.

DMF refers to dimethylformamide.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

IR refers to infrared spectroscopy.

NMR refers to nuclear (proton) magnetic resonance spectroscopy, chemical shifts are reported in ppm (d) downfield from tetramethylsilane.

-φ refers to phenyl ($C_6H_5$).

MS refers to mass spectrometry expressed as m/e, m/z or mass/charge unit. [M+H]$^+$ refers to the positive ion of a parent plus a hydrogen atom. EI refers to electron impact. CI refers to chemical ionization. FAB refers to fast atom bombardment.

HRMS refers to high resolution mass spectrometry.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1

1-[4-(Phenylsulfonyl)phenyl]hydrazine (V)

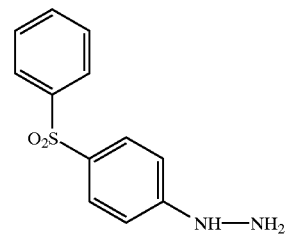

A mixture of 4-chlorophenyl phenyl sulfone (10.1 g, 40.0 mmol), hydrazine mono hydrate (30 mL), and triethylamine (4 drops) in ethylene glycol (20 mL) is heated at 150° for 15 hr. Upon cooling, the mixture is diluted with $H_2O$ and filtered. The residual solid is washed with $H_2O$ until the washings are neural (pH=6). This material is then triturated with methylene chloride and dried under reduced pressure at 50° to give the title compound, IR (drift) 3282, 1586, 1514, 1306, 1291, 1158, 1145, 1104, 996, 813, 756, 730, 717, 688 and 678 cm$^{-1}$, NMR (300 MHz, CDCl$_3$) 7.70–7.85, 7.45–7.65, 6.79 and 4.22 δ; MS (EI) m/z 248 (M$^+$), 125, 123, 108, 107, 90, 80, 77, 63 and 51.

Preparation 2

1-[4-[(4-Fluorophenyl)sulfonyl]phenyl]hydrazine (V)

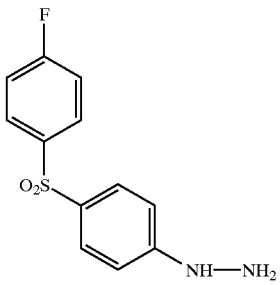

Step I: 4-Fluorophenyl-4-nitrophenyl sulfide (III)

A mixture of 4-fluorothiophenol (I, 2.08 g, 19.5 mmol), 1-chloro-4-nitrobenzene (II, 3.39 g, 21.5 mmol), and potassium carbonate (5.40 g, 39.0 mmol) in acetonitrile (75 mL) is stirred at 20–25° under nitrogen for 16 hr. The mixture is diluted with $H_2O$ (100 mL) and extracted into methylene chloride (3×100 mL). The extracts are dried over anhydrous magnesium sulfate, filtered, and concentrated under reduced pressure to provide a quantitative yield of the desired thioether, mp=84–90°; NMR (300 MHz, $CDCl_3$) 8.07, 7.45–7.60 and, 7.05–7.25 δ.

Step II: 4-[(4-Fluorophenyl)sulfonyl]phenylamine (IV)

A hot mixture (100°) of 4-fluorophenyl 4-nitrophenyl sulfide (III, Step I, 1.91 g, 7.66 mmol) in glacial acetic acid (50 mL) is treated with hydrogen peroxide (30%, 2.60 mL), followed 20 min later by a second portion of hydrogen peroxide (30%, 1.70 mL). The mixture continued to heat for an additional 30 min, and is then allowed to cool to 20–25°. The mixture is concentrated to near dryness and filtered, rinsing the solid with $H_2O$. The solid is dried in a vacuum oven at 50° to give the intermediate sulfone, IR (drift) 1590, 1534, 1356, 1307, 1294, 1242, 1166, 1156, 1109, 1101, 858, 839, 742, 687 and 665 $cm^{-1}$; NMR (300 MHz, $CDCl_3$) 8.35, 8.12, 7.95–8.05 and 7.15–7.30 δ; MS (EI) m/z 281 ($M^+$), 159, 143, 111, 95, 95, 83, 76, 74 and 51.

A mixture of 4-fluorophenyl 4-nitrophenyl sulfone (1.89 g, 6.72 mmol) in methanol (80 mL) is treated with Rhodium on carbon (5%, 95 mg) and hydrogenated at 20 psi for 24 hr. The mixture is filtered, rinsing with methylene chloride (2×100 mL) and methanol (100 mL). The filtrate is concentrated to near dryness and refiltered, rinsing with minimal methanol. The solid is dried in the vacuum oven at 50° to give the desired amine, mp=204–205°: IR (drift) 3473, 3373, 1638, 1592, 1489, 1303, 1294, 1285, 1231, 1159, 1144, 1107, 834, 713 and 689 $cm^{-1}$; NMR (300 MHz, $CDCl_3$) 7.80–7.95, 7.60–7.75, 7.13, 6.60–6.75 and 4.17 δ; MS (EI) m/z 251 ($M^+$), 140, 108, 95, 92, 80, 65, 65, 63 and 51.

Step III: 1-[4-[(4-fluorophenyl)sulfonyl]phenyl]hydrazine (V)

A mixture of 4-[(4-fluorophenyl)sulfonyl]phenylamine (IV, Step II, 3.10 g, 12.3 mmol) in concentrated hydrochloric acid (30 mL) at 0° is treated with sodium nitrite (934 mg, 13.5 mmol) in $H_2O$ (15 mL). After 30 min, the mixture is treated with stannous chloride (5.57 g, 24.7 mmol) in concentrated hydrochloric acid (15 mL). The mixture is stirred at 0° for 1 hr, and then at 20–25° for 1 hr. The precipitate is collected and slurried in $H_2O$. The mixture is made basic (sodium hydroxide, 50%) and the solid isolated. The material is partitioned between methylene chloride and saline. The organic layer is dried, filtered, and concentrated under reduced pressure to give the title compound, NMR (300 MHz, $CDCl_3$) 7.85–7.95, 7.74, 7.13, 6.85, 5.64 and 3.65 δ.

Example 1

9-(Phenylsulfonyl)-1,2,3,4,5,6-hexahydroazepino[4,5-b]indole (IX)

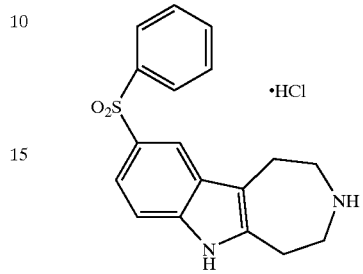

Step I: 1-Benzyl-4-azepanone N-[4-(phenylsulfonyl)phenyl]hydrazone (VII)

A mixture of 1-[4-(phenylsulfonyl)phenyl]hydrazine (V, PREPARATION 1, 7.06 g, 28.4 mmol) and 4-benzylazapanone (VI, 5.78 g, 28.4 mmol) in ethanol (130 mL) is treated with glacial acetic acid (8 drops) and heated at reflux for 1 hr. Upon cooling, the precipitate is collected, washed with ethanol and dried in the vacuum oven at 50° to give the desired compound, mp=142–146°. The filtrate is concentrated and purified via flash chromatography (ethyl acetate/heptane; 65/35) to provide additional product as two regioisomers. Analytical data for one isomer: IR (drift) 1593, 1511, 1323, 1301, 1261, 1148, 1106, 1069, 833, 758, 748, 735, 709, 689 and 600 $cm^{-1}$; NMR (300 MHz, $CDCl_3$) 7.85–7.95, 7.77, 7.40–7.65, 7.15–7.35, 7.06, 3.65, 2.65–2.85, 2.55–2.65, 2.35–2.45 and, 1.70–1.85; MS (EI) m/z 433 ($M^+$), 186, 120, 108, 97, 96, 91, 82, 77, 65 and 51. Analytical data for the slower eluting isomer: IR (drift) 1593, 1509, 1324, 1296, 1285, 1264, 1148, 1106, 1085, 1069, 834, 735, 710, 688 and 605 $cm^{-1}$; NMR (300 MHz, $CDCl_3$) 7.85–7.95, 7.70–7.85, 7.35–7.55, 7.15–7.35, 7.06, 3.60, 2.55–2.75, 3.32–2.45 and 1.85–2.00; MS (EI) m/z 433 ($M^+$), 187, 186, 120, 108, 97, 91, 82, 77, 65 and 51.

Step II: 3-Benzyl-9-(phenylsulfonyl)-1,2,3,4,5,6-hexahydroazepino[4,5-b]indole (VIII)

A mixture of 1-benzyl-4-azepanone N-[4-(phenylsulfonyl)phenyl]hydrazone (VII, Step I, 3.41 g, 7.86 mmol) and polyphosporic acid (4.78 g) in o-xylene (550 mL) is heated at 100° under nitrogen for 3 hr. Upon cooling, the xylene is decanted and the residual material partitioned between methylene chloride/methanol and sodium hydroxide (0.5 M). The phases are separated and the aqueous layer is further extracted with more methylene chloride/methanol (2×). The organic phases are combined and dried over anhydrous magnesium sulfate, filtered, and concentrated under reduced pressure to give an oil. The oil is purified by flash chromatography (Biotage 40M; ethyl acetate/heptane, 7/3) to give the desired indole, mp=86–88°, dec; IR (drift) 3343, 2910, 1475, 1449, 1337, 1301, 1146, 1131, 1090, 748, 731, 719, 698, 688 and 627 $cm^{-1}$; NMR (300 MHz, $CDCl_3$) 8.10–8.20, 8.06, 7.96, 7.66, 7.25–7.55, 3.85 and 2.90–3.05 δ; MS (EI) m/z 416 ($M^+$), 296, 154, 146, 134, 134, 132, 120, 91 and 65.

Step III: 9-(Phenylsulfonyl)-1,2,3,4,5,6-hexahydroazepino[4,5-b]indole (IX)

A mixture of 3-benzyl-9-(phenylsulfonyl)-1,2,3,4,5,6-hexahydroazepino[4,5-b]indole (VIII, Step II, 453 mg, 1.09 mmol) in methanol (50 mL) is treated with palladium hydroxide (118 mg) and hydrogenated at 30 psi for 5 days. The mixture is filtered, rinsing with methanol and methylene chloride, and the filtrate concentrated under reduced pressure to give an amorphous solid. The material is purified by flash chromatography (Biotage 40M; methanol/methylene chloride, 5/95; methanol/methylene chloride/ammonium hydroxide, 20/79/1) to give the title compound. Analytical data for the hydrochloride salt, mp=290–291.5°; IR (drift) 3382, 2751, 2698, 2689, 2646, 2438, 1297, 1150, 1131, 1095, 801, 759, 722, 684 and 616 cm$^{-1}$; NMR (300 MHz, DMSO-d$_6$) 11.65, 7.35, 8.05–8.15, 7.85–7.95, 7.40–7.65, 3.20–3.40 and 3.10–3.25 δ; MS (EI) m/z 326 (M$^+$), 298, 297, 286, 285, 284, 143 and 77; HRMS (FAB) calculated for $C_{18}H_{19}N_2O_2S=327.1167$, found 327.1165.

Example 2

9-[(4-Fluorophenyl)sulfonyl]-1,2,3,4,5,6-hexahydroazepino[4,5-b]indole (IX)

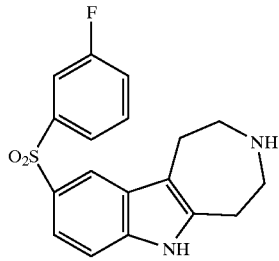

Following the general procedure of EXAMPLE 1 (Steps I–III) and making non-critical variations, 1-[4-[(4-fluorophenyl)sulfonyl]phenyl]hydrazine (V, PREPARATION 2) is converted to the title compound, mp=168°, dec.; IR (drift) 2923, 1590, 1491, 1475, 1336, 1308, 1287, 1236, 1147, 1131, 1089, 837, 816, 749 and 683 cm$^{-1}$; NMR (300 MHz, CDCl$_3$) 8.05–8.15, 8.05, 7.90–8.00, 7.55–7.65, 7.30–7.35, 7.12, 3.05–3.15 and 2.90–3.00 δ; HRMS (FAB) calculated for $C_{18}H_{18}FN_2O_2S=345.1073$, found 345.1087.

Example 3

9-[(4-Methylphenyl)sulfonyl]-1,2,3,4,5,6-hexahydroazepino[4,5-b]indole (IX)

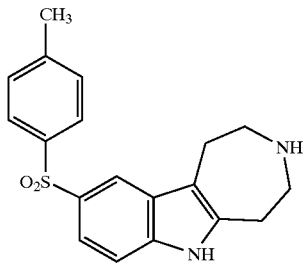

Following the general procedure of EXAMPLE 1 (Steps I–III) and making non-critical variations, 1-[4-[(4-methylphenyl)sulfonyl]phenyl]hydrazine (V, PREPARATION 2) is converted to the title compound, mp=125°, dec; IR (drift) 3027, 2921, 2830, 1475, 1453, 1336, 1298, 1287, 1150, 1130, 1090, 812, 747, 682 and 658 cm$^{-1}$; NMR (300 MHz, CDCl$_3$) 8.12, 7.83, 7.55–7.65, 7.20–7.35, 3.05–3.20, 2.90–3.05 and 2.36 δ; MS (EI) m/z 340 (M$^+$), 311, 298, 154, 144, 143, 115, 91, 91 and 65; HRMS (FAB) calculated for $C_{19}H_{21}N_2O_2S=341.1324$, found 341.1311.

Example 4

9-[(4-Methoxyphenyl)sulfonyl]-1,2,3,4,5,6-hexahydroazepino[4,5-b]indole (IX)

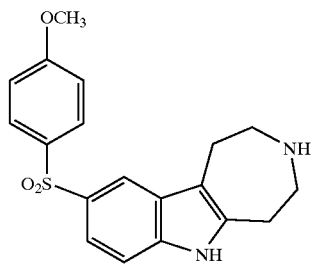

Following the general procedure of EXAMPLE 1, and making non-critical variations, 1-[4-[(4-methylphenyl)sulfonyl]phenyl]hydrazine (V, PREPARATION 2) is converted to the title compound, mp=139°, dec.; IR (drift) 2927, 2837, 1593, 1496, 1335, 1312, 1293, 1260, 1142, 1130, 1092, 834, 802, 748 and 683 cm$^{-1}$; NMR (300 MHz, DMSO-d$_6$) 11.30, 7.90–8.00, 7.75–7.85, 7.40–7.50, 7.30–7.40, 7.00–7.10, 3.77 and 2.75–3.05; MS (EI) m/z 356 (M$^+$), 327, 314, 155, 154, 143, 143, 115, 77 and 57; HRMS (FAB) calculated for $C_{19}H_{21}N_2O_3S=357.1273$, found 357.1275.

Example 5

9-[(3-Fluorophenyl)sulfonyl]-1,2,3,4,5,6-hexahydroazepino[4,5-b]indole (IX)

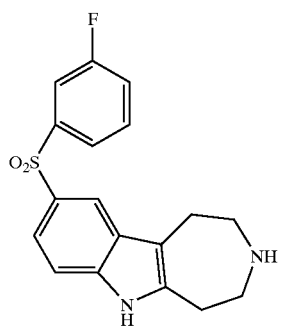

Following the general procedure of EXAMPLE 1, and making non-critical variations, 1-[4-[(3-fluorophenyl)sulfonyl]phenyl]hydrazine (V, PREPARATION 2) is converted to the title compound, mp=153–156°: IR (drift) 2926, 2867, 2855, 1474, 1311, 1296, 1225, 1151, 1129, 1082, 773, 742, 698, 677 and 629 cm$^{-1}$; NMR (300 MHz, DMSO-d$_6$) 11.37, 8.00–8.10, 7.70–7.80, 7.30–7.75 and 2.75–2.95 δ; MS (EI) m/z 344 (M$^+$), 315, 302, 154, 144, 143, 128, 128, 115 and 73; HRMS (FAB) calculated for $C_{18}H_{18}FN_2O_2S=345.1073$, found 345.1075.

Example 6

9-[(3-Methoxylphenyl)sulfonyl]-1,2,3,4,5,6-hexahydroazepino[4,5-b]indole hydrochloride (IX)

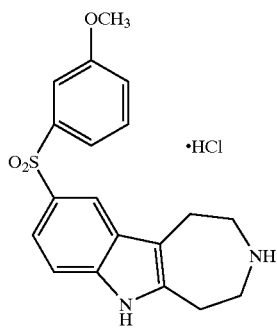

Following the general procedure of EXAMPLE 1, and making non-critical variations, 1-[4-[(3-methoxyphenyl)sulfonyl]phenyl]hydrazine (V, PREPARATION 2) is converted to the title compound, mp=232–235°, dec.; IR (drift) 2976, 2963, 2832, 2805, 2770, 2739, 1475, 1303, 1248, 1151, 1141, 746, 694, 682 and 629 cm$^{-1}$; NMR (300 MHz, DMSO-d$_6$) 11.63, 9.31, 8.10–8.15, 7.35–7.60, 7.10–7.20, 3.79, 3.20–3.40 and 3.05–3.40 δ; MS (EI) m/z 356 (M$^+$), 327, 314, 107, 74, 73, 59, 57, 57 and 56; MS (FAB) m/z 357 (MH$^+$), 356, 328, 177, 155, 121, 103, 89; HRMS (FAB) calculated for C$_{19}$H$_{21}$N$_2$O$_3$S=357.1273, found 357.1277.

Example 7

9-[(4-Trifluoromethyphenyl)sulfonyl]-1,2,3,4,5,6-hexahydroazepino[4,5-b]indole hydrochloride (IX)

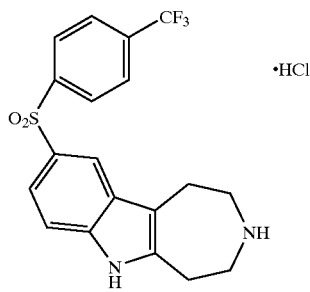

Following the general procedure of EXAMPLE 1, and making non-critical variations, 1-[4-[(4-trifluoromethylphenyl)sulfonyl]phenyl]hydrazine (V, PREPARATION 2) is converted to the title compound, mp=278–279°, dec.; IR (drift) 2773, 2756, 2732, 1321, 1306, 1178, 1156, 1133, 1122, 1108, 1061, 844, 716, 623 and 618 cm$^{-1}$; NMR (300 MHz, DMSO-d$_6$) 8.05–8.20, 7.90–8.00, 7.55–7.45, 7.45–7.55 and 3.05–3.40 δ; MS (EI) m/z 394 (M$^+$), 365, 352, 154, 143, 73, 71, 59, 58 and 57.

Example 8

6-Ethyl-9-(phenylsulfonyl)-1,2,3,4,5,6-hexahydroazepino[4,5-b]indole (IX)

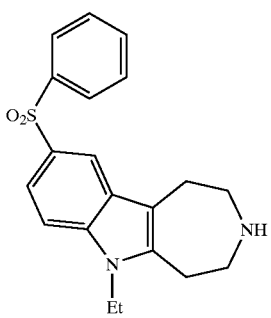

Step I: 3-Benzyl-6-ethyl-9-(phenylsulfonyl)-1,2,3,4,5,6-hexahydroazepino[4,5-b]indole A 0° mixture of 3-benzyl-9-(phenylsulfonyl)-1,2,3,4,5,6-hexahydroazepino[4,5-b]indole (EXAMPLE 1, Step II, 301 mg, 0.723 mmol) in dry DMF (5 mL) is treated with sodium hydride (60% in oil, 32 mg, 0.795 mmol), and allowed to warm to 20–25° over 1.5 hr. The mixture is then cooled (0°), treated with iodoethane (64 μL, 0.795 mmol) and allowed to slowly warm to 20–25° under nitrogen over 72 hr. The resultant mixture is diluted with ethyl acetate (50 mL) and washed with H$_2$O (3×25 mL) and saline (25 mL). The organic layer is dried over anhydrous magnesium sulfate, filtered, and concentrated under reduced pressure to give a solid. The solid is purified via chromatography (20 g SG; ethyl acetate/heptane, 65/35) to give the indole as a solid, mp=188–191°; IR (drift) 1477, 1373, 1300, 1289, 1157, 1148, 1094, 766, 756, 738, 728, 701, 694, 645 and 621 cm$^{-1}$; NMR (300 MHz, CDCl$_3$) 8.10–8.20, 7.90–8.05, 7.65–7.75, 7.20–7.50, 4.11, 3.82, 2.85–3.05 and 1.27 δ; MS (EI) m/z 444 (M$^+$), 326, 324, 312, 167, 154, 132, 118, 96, 91 and 64.

Step II: 6-Ethyl-9-(phenylsulfonyl)-1,2,3,4,5,6-hexahydroazepino[4,5-b]indole (X)

A mixture of 3-benzyl-6-ethyl-9-(phenylsulfonyl)-1,2,3,4,5,6-hexahydroazepino[4,5-b]indole (Step I, 107 mg, 0.241 mmol) in methanol (20 mL, 1 drop concentrated hydrochloric acid) is treated with palladium on carbon (10%, 32 mg) and hydrogenated at 25 psi for 48 hr. The resulting mixture is filtered, rinsing with methanol and methylene chloride, and the filtrate is concentrated to a solid. The solid is purified via chromatography (10 g SG; methanol/methylene chloride/ammonium hydroxide, 20/79/1) to give the title compound, mp=224°, dec.; IR (drift) 2982, 2935, 2743, 1473, 1449, 1312, 1300, 1151, 1091, 819, 768, 728, 691, 647 and 623 cm$^{-1}$; NMR (300 MHz, DMSO-d$_6$) 8.09, 7.85–7.95, 7.45–7.65, 4.20, 2.95–3.25 and 1.15 δ; MS (EI) m/z 354 (M$^+$), 312, 170, 167, 153, 143, 114, 78, 76 and 51; HRMS (FAB) calculated for C$_{20}$H$_{23}$N$_2$O$_2$S=355.1480, found 355.1488.

Example 9

6-Ethyl-9-[(4-fluorophenyl)sulfonyl]-1,2,3,4,5,6-hexahydroazepino[4,5-b]indole hydrochloride (IX)

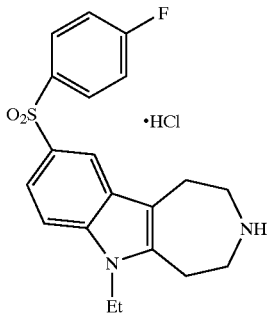

Following the general procedure of EXAMPLE 8, and making non-critical variations, 3-benzyl-9-[(4-fluorophenyl)sulfonyl]-1,2,3,4,5,6-hexahydroazepino[4,5-b]indole (EXAMPLE 2) is converted to the title compound, mp=227–233°, dec.; IR (drift) 2972, 2834, 2755, 2713, 2679, 1589, 1490, 1471, 1312, 1293, 1223, 1148, 1094, 715 and 693 cm$^{-1}$; MS (EI) m/z 372 (M$^+$), 331, 330, 171, 171, 154, 143, 143, 91 and 57; NMR (300 MHz, DMSO-d$_6$) 9.30, 8.18, 8.02, 7.55–7.70, 7.41, 4.24, 3.10–3.40 and 1.19 δ; MS (FAB) m/z 373 (MH$^+$), 372, 371, 344 and 330; HRMS (FAB) calculated for $C_{20}H_{22}FN_2O_2S$=373.1386, found 373.1371.

Example 10

6-Methyl-9-[(4-fluorophenyl)sulfonyl]-1,2,3,4,5,6-hexahydroazepino[4,5-b]indole hydrochloride (IX)

Following the general procedure of EXAMPLE 8, and making non-critical variations, 3-benzyl-9-[(4-fluorophenyl)sulfonyl]-1,2,3,4,5,6-hexahydroazepino[4,5-b]indole (EXAMPLE 2) is converted to the title compound, mp>300°; IR (drift) 2775, 1589, 1489, 1310, 1288, 1237, 1149, 1091, 841, 836, 805, 718, 667, 639 and 605 cm$^{-1}$; NMR (300 MHz, DMSO-d$_6$) 9.51, 8.17, 8.01, 7.63, 7.41, 3.72 and 3.10–3.45 δ.

Example 11

6-Methyl-9-[(4-trifluoromethylphenyl)sulfonyl]-1,2,3,4,5,6-hexahydroazepino[4,5-b]indole hydrochloride (IX)

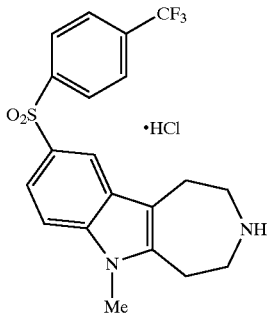

Following the general procedure of EXAMPLE 8, and making non-critical variations, 3-benzyl-9-[(4-trifluoromethyl)phenyl]sulfonyl-1,2,3,4,5,6-hexahydroazepino[4,5-b]indole (EXAMPLE 7) is converted to the title compound, mp=286°, dec.; IR (drift) 2740, 2716, 1321, 1309, 1187, 1172, 1155, 1132, 1109, 1098, 1063, 845, 719, 648 and 625 cm$^{-1}$; NMR (300 MHz, DMSO-d$_6$) 9.31, 8.19, 8.13, 7.93, 7.64, 3.71 and 3.10–3.40 δ.

Example 12

6-Ethyl-9-[(4-trifluoromethylphenyl)sulfonyl]-1,2,3,4,5,6-hexahydroazepino[4,5-b]indole hydrochloride (IX)

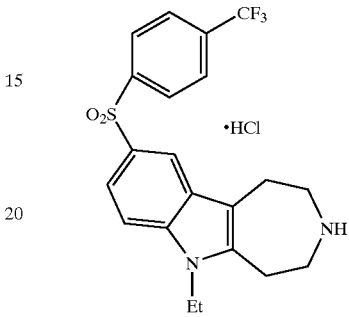

Following the general procedure of EXAMPLE 8, and making non-critical variations, 3-benzyl-9-[(4-trifluoromethylphenyl)sulfonyl]-1,2,3,4,5,6-hexahydroazepino[4,5-b]indole (EXAMPLE 7) is converted to the title compound, mp=170–179°, dec.; IR (drift) 2762, 1326, 1302, 1294, 1190, 1184, 1171, 1153, 1138, 1109, 1095, 1064, 830, 716 and 618 cm$^{-1}$; NMR (300 MHz, DMSO-d$_6$) 9.40, 8.20, 8.14, 7.93, 7.65, 4.15–4.30, 3.10–3.45 and 1.10–1.20 δ.

Example 13

6-Methyl-9-(phenylsulfonyl)-1,2,3,4,5,6-hexahydroazepino[4,5-b]indole hydrochloride (IX)

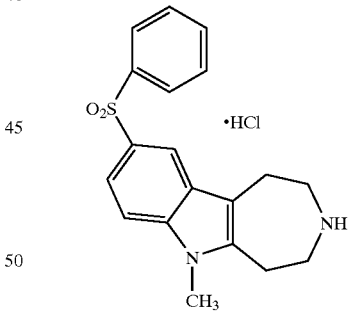

Step I: 1-Benzoyl-4-azepanone N-[4-(phenylsulfonyl)phenyl]hydrazone

A mixture of 1-[4-(phenylsulfonyl)phenyl]hydrazine (2.05 g, 8.26 mmol) and 4-benzoylazapanone (1.97 g, 9.09 mmol) in ethanol (40 mL) is treated with glacial acetic acid (8 drops) and heated at reflux for 1 hr. Upon cooling, the precipitate is collected, washed with ethanol and dried in the vacuum oven (50°) to give the desired hydrazone, mp=202–204°.

Step II: 3-Benzoyl-9-(phenylsulfonyl)-1,2,3,4,5,6-hexahydroazepino[4,5-b]indole

A mixture of 1-benzoyl-4-azepanone N-[4-(phenylsulfonyl)phenyl]hydrazone (Step I, 2.00 g, 4.47 mmol) in dichloroethane/phosphoric acid 84% (1/1, 40 mL)

is heated at reflux for 16 hr. Upon cooling, the product is diluted with saline and extracted into methylene chloride (3×). The extracts are dried, filtered, and concentrated under reduced pressure to give a solid. The solid is purified via silica gel chromatography (Biotage 40M; ethyl acetate/heptane, 75/25) to give the desired indole.

Step III: 3-Benzoyl-6-methyl-9-(phenylsulfonyl)-1,2,3,4,5,6-hexahydroazepino[4,5-b]indole A 0° mixture of 3-benzoyl-9-(phenylsulfonyl)-1,2,3,4,5,6-hexahydroazepino[4,5-b]indole (Step II, 1.61 g, 3.74 mmol) in dry DMF (18 mL) is treated with sodium hydride (60% in oil, 165 mg, 4.11 mmol). After 30 min, the mixture is treated with iodomethane (256 μL, 4.11 mmol) and allowed to slowly warm to 20–25° under nitrogen over 16 hr. The resultant mixture is diluted with $H_2O$ and filtered. The residual solid is triturated with refluxing methanol, isolated, and dried in the vacuum oven at 50° to give the desired indole, mp=254–255°.

Step IV: 6-Methyl-9-(phenylsulfonyl)-1,2,3,4,5,6-hexahydroazepino[4,5-b]indole hydrochloride A mixture of 3-benzoyl-9-(phenylsulfonyl)-1,2,3,4,5,6-hexahydroazepino[4,5-b]indole (Step III, 1.25 g, 2.81 mmol) and potassium hydroxide (1.58 g, 28.1 mmol) in ethylene glycol (30 mL) is heated at 130° under nitrogen for 92 hr. Upon cooling, the mixture is diluted with $H_2O$ and extracted into ethyl acetate (3×). The combined extracts are washed with $H_2O$ (2×) and saline, dried over anhydrous magnesium sulfate, filtered, and concentrated under reduced pressure to give a solid. The solid is dissolved in hot methylene chloride/methanol and treated with methanolic hydrochloric acid. The resultant mixture is concentrated and crystallized from ethyl acetate/methanol to give the title compound, mp>300°; IR (drift) 2820, 2792, 2747, 2717, 2704, 2665, 2651, 1299, 1147, 1096, 803, 729, 687, 643 and 621 cm$^{-1}$; NMR (300 MHz, DMSO-d$_6$) 9.41, 8.13, 7.85–7.95, 7.50–7.65, 3.70 and 3.10–3.40 δ; MS (EI) m/z 340 (M$^+$), 298, 157, 156, 128, 78, 74, 73, 58 and 57; HRMS (FAB) calculated for $C_{19}H_{21}N_2O_2S$=341.1324, found=341.1319.

Example 14

9-[(3,4-Difluorophenyl)sulfonyl]-1,2,3,4,5,6-hexahydroazepino[4,5-b]indole (IX)

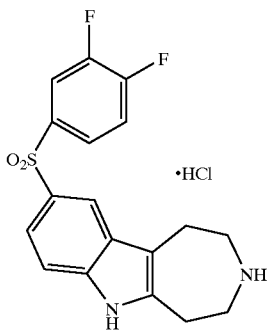

Following the general procedure of EXAMPLE 1 (steps I–III) and making non-critical variations, 1-[4-[(3,4-difluorophenyl)sulfonyl]phenyl]hydrazine (V, PREPARATION 2) is converted to the title compound, mp=320°, dec; IR (drift) 2732, 1507, 1310, 1293, 1277, 1147, 1128, 1116, 1072, 800, 751, 686, 627, 622 and 610 cm$^{-1}$; NMR (300 MHz, DMSO-d$_6$) δ 11.75, 9.50, 8.10–8.20, 7.75–7.85, 7.55–7.70, 7.40–7.50, 3.25–3.40 and 3.10–3.25; OAMS (supporting ions at): ESI+ 363.1, ESI− 361.0.

Example 15

9-[(3,5-Difluorophenyl)sulfonyl]-1,2,3,4,5,6-hexahydroazepino[4,5-b]indole (IX)

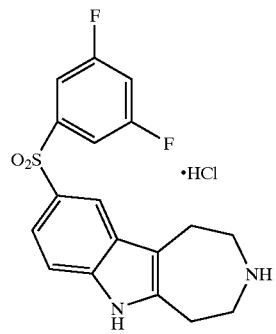

Following the general procedure of EXAMPLE 1 (steps I–III) and making non-critical variations, 1-[4-[(3,5-difluorophenyl)sulfonyl]phenyl]hydrazine (V, PREPARATION 2) is converted to the title compound, mp=313–315°, dec; IR (drift) 3256, 1606, 1591, 1307, 1285, 1269, 1153, 1138, 1122, 983, 850, 795, 678, 666 and 618 cm$^{-1}$; NMR (300 MHz, DMSO-d$_6$) δ 11.70, 9.35, 8.15–8.25, 7.40–7.85 and 3.10–3.40; MS (EI) m/z 362 (M$^+$), 333, 320, 154, 142, 127, 115, 113, 92 and 63.

Example 16

9-[(3,5-Difluorophenyl)sulfonyl]-6-methyl-1,2,3,4,5,6-hexahydroazepino[4,5-b]indole hydrochloride (IX)

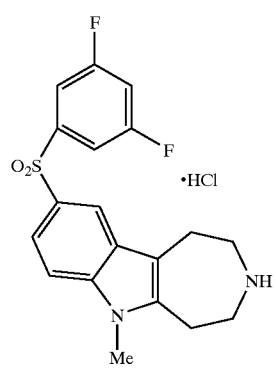

Following the general procedure of EXAMPLE 13 (steps I–IV) and making non-critical variations, 1-[4-[(3,5-difluorophenyl)sulfonyl]phenyl]hydrazine (V, PREPARATION 2) (EXAMPLE 2) is converted to the title compound, mp=337–340°, dec; IR (drift) 2767, 2750, 1603, 1437, 1308, 1295, 1144, 1129, 988, 807, 709, 681, 675, 650 and 627 cm$^{-1}$; NMR (300 MHz, DMSO-d$_6$) δ 9.35, 8.20–8.30, 7.60–7.80, 3.71 and 3.15–3.45; MS (EI) m/z 376 (M$^+$), 334, 334, 156, 114, 113, 64, 63, 57, 52 and 51; HRMS (FAB) calculated for $C_{19}H_{19}F_2N_2O_2S$=377.1135, found=377.1125.

Example 17

9-[(4-(2-Hydroxyethoxy)phenyl)sulfonyl]-6-methyl-1,2,3,4,5,6-hexahydroazepino[4,5-b]indole hydrochloride (IX)

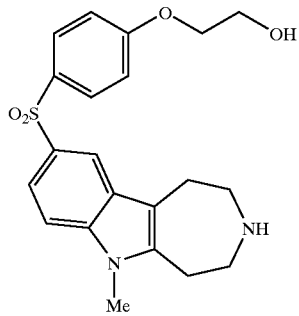

Following the general procedure of EXAMPLE 13 (steps I–IV) and making non-critical variations, 1-[4-[(4-fluorophenyl)sulfonyl]phenyl]hydrazine (V, PREPARATION 2) is converted to the title compound, mp=285–287°, dec; IR (drift) 2957, 2835, 2811, 2760, 1592, 1492, 1458, 1309, 1293, 1261, 1142, 1092, 721, 637 and 618 cm$^{-1}$; NMR (300 MHz, DMSO-d$_6$) δ 9.43, 8.09, 7.81, 7.57, 7.06, 4.85–4.95, 3.95–4.05, 3.69 and 3.00–3.45; MS (EI) m/z 400 (M$^+$), 86, 84, 77, 73, 72, 71, 58, 57, 56 and 51; HRMS (FAB) calculated for $C_{21}H_{25}N_2O_4S$=401.1535, found=401.1540.

Example 18

3,6-Dimethyl-9-(phenylsulfonyl)-1,2,3,4,5,6-hexahydroazepino[4,5-b]indole (X)

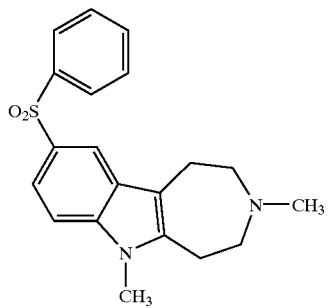

A mixture of 6-methyl-9-(phenylsulfonyl)-1,2,3,4,5,6-hexahydroazepino[4,5-b]indole (EXAMPLE 13, 341 mg, 1.00 mmol) in acetonitrile (5 mL) is treated with formaldehyde (37%, 0.400 mL, 5.00 mmol), sodium cyanoborohydride (101 mg, 1.60 mmol) and glacial acetic acid (1 drop). After 5 hr, the mixture is diluted with ethyl acetate and then washed with water and saline. The organic layer is dried, filtered, and concentrated. The concentrate is dissolved in methylene chloride/methanol and treated with methanolic hydrochloric acid. The solvent is then removed and the residual solid crystallized from hot ethyl acetate/methanol to give the title compound, mp=283–286°; IR (drift) 2523, 2477, 2453, 2428, 1479, 1311, 1304, 1283, 1150, 1094, 756, 730, 694, 644 and 623 cm$^{-1}$; NMR (300 MHz, DMSO-d$_6$) δ 11.00, 8.16, 7.85–7.95, 7.50–7.65, 3.70, 3.15–3.45 and 2.89; MS (FAB) m/z 355 (MH$^+$), 354, 353, 58 and 44; HRMS (FAB) calculated for $C_{20}H_{23}N_2O_2S$=355.1480, found=355.1488.

Example 19

3-Methyl-9-(phenylsulfonyl)-1,2,3,4,5,6-hexahydroazepino[4,5-b]indole (X)

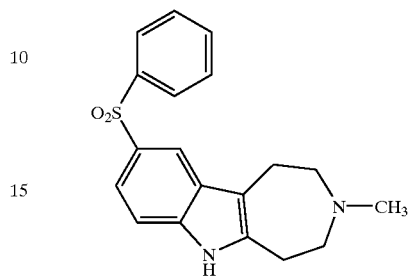

Following the general procedure of EXAMPLE 18, and making non-critical variations, 9-(phenylsulfonyl)-1,2,3,4,5,6-hexahydroazepino[4,5-b]indole (EXAMPLE 1) is converted to the title compound, mp=150°, dec; IR (drift) 2623, 1474, 1447, 1338, 1301, 1173, 1152, 1129, 1090, 755, 741, 719, 689, 673 and 615 cm$^{-1}$; NMR (300 MHz, DMSO-d$_6$) δ 11.68, 8.14, 7.85–7.95, 7.40–7.65, 3.10–3.45 and 2.88; MS (EI) m/z 340 (M$^+$), 296, 77, 74, 73, 72, 71, 58, 57, 56 and 51; HRMS (FAB) calculated for $C_{19}H_{21}N_2O_2S$=341.1324, found=341.1331.

Example 20

9-[(4-fluorophenyl)sulfonyl]-3-isopropyl-6-methyl-1,2,3,4,5,6-hexahydroazepino[4,5-b]indole (X)

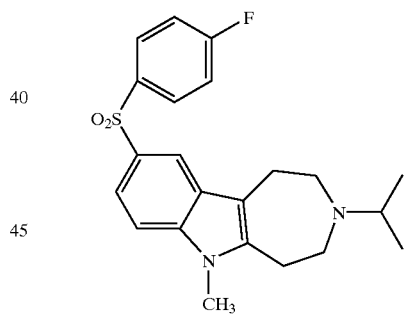

Following the general procedure of EXAMPLE 18, and making non-critical variations, 6-methyl-9-[(4-fluorophenyl)sulfonyl]-1,2,3,4,5,6-hexahydroazepino[4,5-b]indole (EXAMPLE 10)) is converted to the title compound, mp=282–283°, dec; IR (drift) 2479, 2437, 1589, 1490, 1310, 1284, 1239, 1161, 1144, 1092, 838, 809, 718, 677 and 667 cm$^{-1}$; NMR (300 MHz, DMSO-d$_6$) δ 10.60, 8.17, 7.99, 7.62, 7.39, 3.71, 3.10–3.75 and 1.31; MS (EI) m/z 400 (M$^+$), 385, 328, 315, 169, 167, 127, 85, 71, 70 and 56; HRMS (FAB) calculated for $C_{22}H_{26}FN_2O_2S$=401.1699, found=401.1709.

Examples 21–44

Following the general procedure of the above EXAMPLEs, making non-critical variations and starting with the corresponding appropriate starting materials, the following compounds are obtained:

21. 1-Methyl-9-(phenylsulfonyl)-1,2,3,4,5,6-hexahydroazepino[4,5-b]indole
22. 2-Methyl-9-(phenylsulfonyl)-1,2,3,4,5,6-hexahydroazepino[4,5-b]indole
23. 4-Methyl-9-(phenylsulfonyl)-1,2,3,4,5,6-hexahydroazepino[4,5-b]indole
24. 5-Methyl-9-(phenylsulfonyl)-1,2,3,4,5,6-hexahydroazepino[4,5-b]indole
25. 9-[(4-Fluorophenyl)sulfonyl]-1-methyl-1,2,3,4,5,6-hexahydroazepino[4,5-b]indole
26. 9-[(4-Fluorophenyl)sulfonyl]-2-methyl-1,2,3,4.5,6-hexahydroazepino[4,5-b]indole
27. 9-[(4-Fluorophenyl)sulfonyl]-4-methyl-1,2,3,4,5,6-hexahydroazepino[4,5-b]indole
28. 9-[(4-Fluorophenyl)sulfonyl]-5-methyl-1,2,3,4,5,6-hexahydroazepino[4,5-b]indole
29. 1,6-Dimethyl-9-(phenylsulfonyl)-1,2,3,4,5,6-hexahydroazepino[4,5-b]indole
30. 2,6-Dimethyl-9-(phenylsulfonyl)-1,2,3,4,5,6-hexahydroazepino[4,5-b]indole
31. 4,6-Dimethyl-9-(phenylsulfonyl)-1,2,3,4,5,6-hexahydroazepino[4,5-b]indole
32. 5,6-Dimethyl-9-(phenylsulfonyl)-1,2,3,4,5,6-hexahydroazepino[4,5-b]indole
33. 9-[(4-Fluorophenyl)sulfonyl]-1,6-dimethyl-1,2,3,4,5,6-hexahydroazepino[4,5-b]indole
34. 9-[(4-Fluorophenyl)sulfonyl]-2,6-dimethyl-1,2,3,4,5,6-hexahydroazepino[4,5-b]indole
35. 9-[(4-Fluorophenyl)sulfonyl]-4,6-dimethyl-1,2,3,4,5,6-hexahydroazepino[4,5-b]indole
36. 9-[(4-Fluorophenyl)sulfonyl]-5,6-dimethyl-1,2,3,4,5,6-hexahydroazepino[4,5-b]indole
37. 9-[(3,5-Difluorophenyl)sulfonyl]-1-methyl-1,2,3,4,5,6-hexahydroazepino[4,5-b]indole
38. 9-[(3,5-Difluorophenyl)sulfonyl]-2-methyl-1,2,3,4,5,6-hexahydroazepino[4,5-b]indole
39. 9-[(3,5-Difluorophenyl)sulfonyl]-4-methyl-1,2,3,4,5,6-hexahydroazepino[4,5-b]indole
40. 9-[(3,5-Difluorophenyl)sulfonyl]-5-methyl-1,2,3,4,5,6-hexahydroazepino[4,5-b]indole
41. 9-[(3,5-Difluorophenyl)sulfonyl]-1,6-dimethyl-1,2,3,4,5,6-hexahydroazepino[4,5-b]indole
42. 9-[(3,5-Difluorophenyl)sulfonyl]-2,6-dimethyl-1,2,3,4,5,6-hexahydroazepino[4,5-b]indole
43. 9-[(3,5-Difluorophenyl)sulfonyl]-4,6-dimethyl-1,2,3,4,5,6-hexahydroazepino[4,5-b]indole
44. 9-[(3,5-Difluorophenyl)sulfonyl]-5,6-dimethyl-1,2,3,4,5,6-hexahydroazepino[4,5-b]indole

CHART A

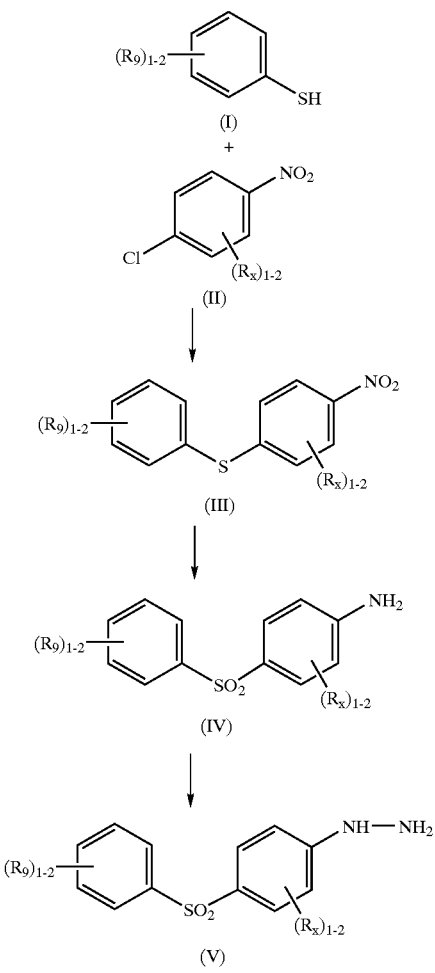

CHART B

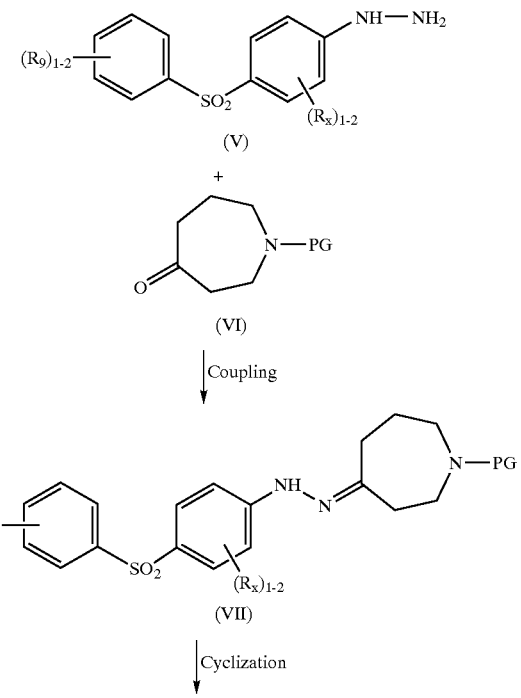

23
-continued

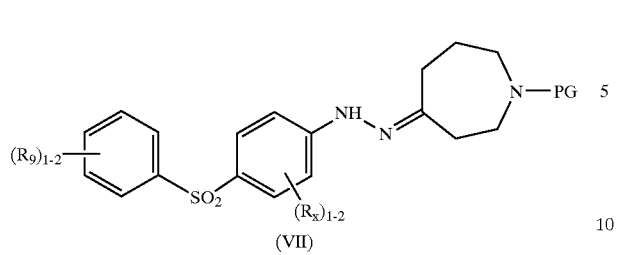

(VII)

↓ Cyclization

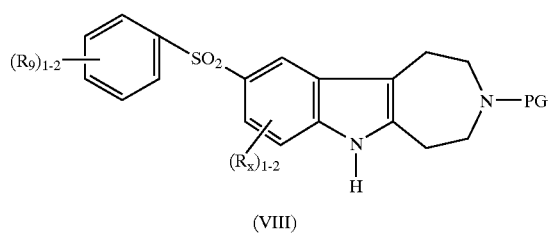

(VIII)

↓ Deprotection

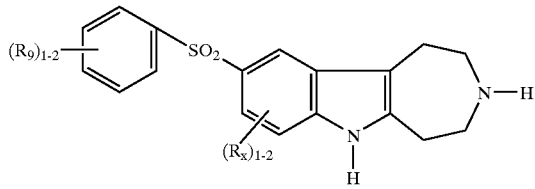

(IX)

↓

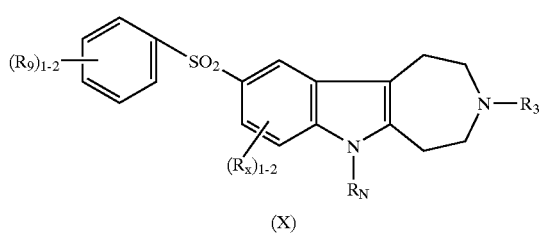

(X)

CHART C

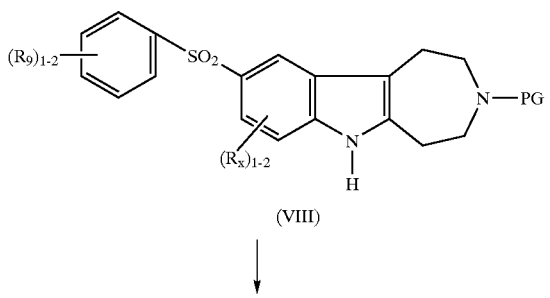

(VIII)

↓

24
-continued

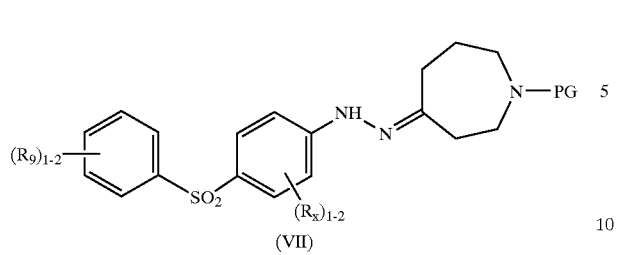

(XI)

↓

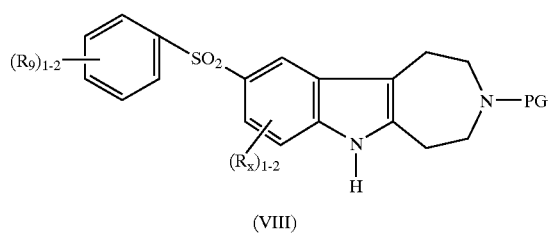

(X)

We claim:

1. A compound of the formula (VII)

(VII)

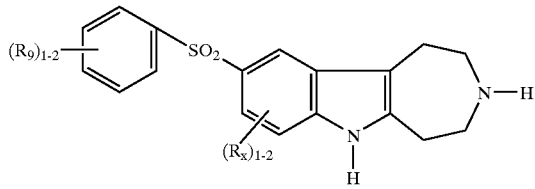

where PG is selected from the group consisting of φ-CH$_2$—, φ-CO—, φ-CH$_2$—CO$_2$— and —CO—O—C(CH$_3$)$_3$, where R$_X$ is:
(1) —H
(2) —F, —Cl, —Br, —I,
(3) —O—R$_{X-1}$ where R$_{X-1}$ is:
 —H,
 C$_1$–C$_4$ alkyl,
 -φ,
(4) —CF$_3$,
(5) —CO—NR$_{X-2}$R$_{X-3}$ where R$_{X-2}$ and R$_{X-3}$ are —H and C$_1$–C$_4$ alkyl, and where R$_{X-2}$ and R$_{X-3}$ are taken with the attached nitrogen atom to form a ring selected from the group consisting of 1-pyrrolidinyl, 1-piperazinyl, 1-morpholinyl,
(6) —NH—SO$_2$—R$_{X-4}$ where R$_{X-4}$ is —H and C$_1$–C$_4$ alkyl,
(7) —NR$_{X-2}$R$_{X-3}$ where R$_{X-2}$ and R$_{X-3}$ are as defined above,
(8) —NR$_{X-4}$—CO—R$_{X-4}$ where R$_{X-4}$ is as defined above,
(9) —SO$_2$—NR$_{X-2}$R$_{X-3}$ where R$_{X-2}$ and R$_{X-3}$ are as defined above,

(10) —C≡N,
(11) —NO$_2$;

where R$_9$ is:
(1) —H,
(2) —F, —Cl,
(3) C$_1$–C$_4$ alkyl,
(4) C$_1$–C$_3$ alkoxy,
(5) —CF$_3$,
(6) C$_0$–C$_4$ alkyl-φ where the -φ substituent is optionally substituted with 1 or 2
  (a) —F, —Cl, —Br, —I,
  (b) —O—R$_{9-1}$ where R$_{9-1}$ is:
    —H,
    C$_1$–C$_4$ alkyl,
    -φ,
  (c) —CF$_3$,
  (d) —CO—NR$_{9-2}$R$_{9-3}$ where R$_{9-2}$ and R$_{9-3}$ are —H and C$_1$–C$_4$ alkyl, and where R$_{9-2}$ and R$_{9-3}$ are taken with the attached nitrogen atom to form a ring selected from the group consisting of 1-pyrrolidinyl, 1-piperazinyl and 1-morpholinyl,
  (e) —NH—SO$_2$—R$_{9-4}$ where R$_{9-4}$ is —H and C$_1$–C$_4$ alkyl,
  (f) —NR$_{9-2}$R$_{9-3}$ where R$_{9-2}$ and R$_{9-3}$ are as defined above,
  (g) —NR$_{9-4}$—CO—R$_{9-4}$ where R$_{9-4}$ is as defined above,
  (h) —SO$_2$—NR$_{9-2}$R$_{9-3}$ where R$_{9-2}$ and R$_{9-3}$ are as defined above,
  (i) —C≡N,
  (j) —NO$_2$
(7) —OR$_{9-1}$ where R$_{9-1}$ is as defined above,
(8) —CO—NR$_{9-2}$R$_{9-3}$ where R$_{9-2}$ and R$_{9-3}$ are as defined above,
(9) —NR$_{9-2}$R$_{9-3}$ where R$_{9-2}$ and R$_{9-3}$ are as defined above,
(10) —NH—SO$_2$—R$_{9-4}$ where R$_{9-4}$ is as defined above,
(11) —NH—CO$_2$—R$_{9-2}$ where R$_{9-2}$ is as defined above.

2. A compound according to claim 1 where PG is φ-CH$_2$— or φ-CO— and where R$_9$ is selected from the group consisting of —H, —F, —Cl, —C$_1$–C$_3$ alkyl, C$_1$–C$_3$ alkoxy and —CF$_3$ and where R$_X$ is selected from the group consisting of —H, —F, —Cl.

* * * * *